United States Patent
Zhai et al.

(10) Patent No.: US 10,829,495 B2
(45) Date of Patent: *Nov. 10, 2020

(54) THIENO-PYRIMIDINE DERIVATIVES AND USES THEREOF

(71) Applicant: ZHEJIANG JIANFENG-YIEN BIOTECHNOLOGY CO., LTD., Jinhua (CN)

(72) Inventors: Haixiao Zhai, Bedford, MA (US); Fan Wu, Brookline, MA (US)

(73) Assignee: ZHEJIANG JIANFENG-YIEN BIOTECHNOLOGY CO., LTD., Jinhua, Zhejiang (CN)

(*) Notice: Subject to any disclaimer, the term of this patent is extended or adjusted under 35 U.S.C. 154(b) by 0 days.

This patent is subject to a terminal disclaimer.

(21) Appl. No.: 15/777,221

(22) PCT Filed: Dec. 1, 2016

(86) PCT No.: PCT/US2016/064502
§ 371 (c)(1),
(2) Date: May 28, 2018

(87) PCT Pub. No.: WO2017/096100
PCT Pub. Date: Jun. 8, 2017

(65) Prior Publication Data
US 2019/0233431 A1  Aug. 1, 2019

Related U.S. Application Data

(60) Provisional application No. 62/262,386, filed on Dec. 3, 2015.

(51) Int. Cl.
*C07D 495/04* (2006.01)
*A61P 37/02* (2006.01)
*A61P 35/00* (2006.01)

(52) U.S. Cl.
CPC ............ *C07D 495/04* (2013.01); *A61P 35/00* (2018.01); *A61P 37/02* (2018.01)

(58) Field of Classification Search
CPC .......................... A61K 31/519; C07D 495/04
USPC ........................................ 514/260.1; 544/278
See application file for complete search history.

(56) References Cited

U.S. PATENT DOCUMENTS

| | | | |
|---|---|---|---|
| 6,503,914 B1 | 1/2003 | Benish et al. | |
| 2010/0216789 A1 | 8/2010 | Nagarathnam et al. | |
| 2015/0045324 A1 | 2/2015 | Cha et al. | |
| 2015/0119379 A1 | 4/2015 | Butterworth et al. | |

OTHER PUBLICATIONS

Wolff et. al., "Burger's Medicinal Chemistry and Drug Discovery," 5th Ed. Part 1, pp. 975-977 (1995).*
Banker, et. al., (1996), Modern Pharmaceuticals, p. 596.*
WO 2007/084815 A2 (Janssen Pharmaceutica, N.V.) Jul. 26, 2007 (Jul. 26, 2007); entire document.
PCT/US2016/064507 International Search Report.
PCT/US2016/064507 Written Opinion of the International Seaching Authority.
Elrazaz et al. "Thieno[2,3-d)pyrimidine based derivatives as kinase inhibitors and anticancer agents" Future Journal of Pharmaceutical Sciences. Sep. 25, 2015 (Sep. 25, 2015).

* cited by examiner

*Primary Examiner* — Jeffrey H Murray
(74) *Attorney, Agent, or Firm* — Duane Morris LLP; Thomas J. Kowalski; Deborah L. Lu

(57) ABSTRACT

Compounds having the general formula I or III, ad pharmaceutical compositions comprising the same. The compounds of the present invention are useful as selective mutant epidermal growth factor receptor tyrosine kinase (EGFR-TK) inhibitor, and for the treatment of EGFR related diseases and disorders such as cancer.

17 Claims, No Drawings

THIENO-PYRIMIDINE DERIVATIVES AND USES THEREOF

FIELD OF THE INVENTION

The present invention relates to cancer treatment, specifically to compositions and methods of inhibiting the epidermal growth factor receptor of cancer cells.

BACKGROUND OF THE INVENTION

The epidermal growth factor receptor (EGFR, Erbb1) is involved in the proliferation of normal and maligant cells. Overexpression of EGFR has been found to relate to cancers such as lung, breast, head & neck, and bladder cancers.

There are four receptor tyrosine kinases in the family of EGFRs: EGFR (ErbB1), human epidermal growth factor receptor 2 (HER2, ErbB2), HER3 (ErbB3), and HER4 (ErbB4). Tyrosine kinases act as a signal transductor. Ligands, outside of cell bind to the ligand-binding domain of the receptor resulting in the formation of active homo- or hetereodimers, autophosphorylation of EGFR and activation of docking proteins (Greulich H. Chen, PLoS Med, 2005, 2, e313; Olayioye M A, EMBO J, 2000, 19, 3159-3167). These signals promote cellular processes such as proliferation, protein synthesis, angiogenesis, cell growth and survival.

Overexpression of EGFR exists in about 70% of cancer patients (Seymour, L. K., Curr Drug Targets, 2001, 2, 117-133). The EGFR tyrosine kinases have been therapeutic targets and several drugs have been developed that inhibit the kinases' activities and block their signal transduction pathway, as ATP competitors, such as FDA approved Tarcevar, Irressa, and Gilotrif (all 4-amino-quinazoline-based inhibitors). These agents have been widely used in EGFR overexpressed non-small cell lung cancer (NSCLC) patients including wild-type and activating mutation patients (W. Pao, Nat. Rev. Cancer, 2010, 10, 760-774; R. Rosell, Lancet Oncol, 2012, 13, 239-246; N. U. Lin, Breast Cancer Res, 2004, 6, 204-210).

There are two common activating mutations among the patients: L858R and delE746-A750. Mechanistic studies demonstrated that the clinical activity of Tarcevar and Iressa on activating mutant patients might be the results of combined effects of enhanced inhibitor binding affinity to the mutant-kinase and addiction of mutant-cell to the oncogene (J A. Engelman, Science, 2007, 316, 1039-1043).

These $1^{st}$ and $2^{nd}$ generation inhibitors with 4-amino-quinazoline-based core structure, however, do not work well on about 50% of patients with replased and acquired resistant diseases, such as NSCLC. The acquired resistance is caused by the mutation of gatekeeper residue of T790M (L V. Sequist, Sci Transl Med, 2011, 3, 75ra26; S. Kobayashi, N Engl J Med, 2005, 352, 786-792; W. Pao, PLoS Med, 2005, 2, 373; JA. Engelman, Semin Respir Crit Care Med, 2005, 26, 314-322). This mutation ($2^{nd}$ mutation) increases the ATP binding affinity to EGFR tyrosine kinase and affects the thermodynamic and kinetic binding characteristics of these inhibitors (C H. Yun, Proc Natl Acad Sci USA, 2008, 105, 2070-2075; Cancer Cell, 2007, 11, 217-227; M. Azam, Nat Struct Mol Biol, 2008, 15, 1109-1118; TA. Carter, Proc Natl Acad Sci USA, 2005, 102, 11011-11016). The bulky methionine side chain in gatekeeper region prevents those drug molecules from the interaction with the ATP-binding pocket at clinically achievable concentrations.

Second generation covalent EGFR inhibitors, such as the FDA approved Gilotrif and a compound on clinical trial, HKI-272, are effective to T790M mutant patients. But Gilotrif is limited to use in activating mutant patients because its dose-limiting toxicities which account for the inhibition of wild-type EGFR.

Therefore there is need to find therapeutic agents which inhibits mutant EGFR selectively without affect the wild-type EGFR.

SUMMARY OF THE INVENTION

The fused pyrimidine derivatives of the present invention satisfy the above need, and are selective and effective inhibitors of mutant epidermal growth factor receptor (EGFR) tyrosine kinases yet without affecting wild-type EGFR, resulting in reduced side effects. The compounds of the present invention are active on the therapeutic targets and are effective for treating diseases related to abnormal activity of EGFR, HER2 activity, such as cancer.

The present invention relates to fused pyrimidine derivatives which selectively and effectively inhibits cancers or tumors with mutant epidermal growth factor receptor (EGFR) tyrosine kinases while not affecting the wild-type EGFR to reduce the side effect.

The compounds of the present invention have the following general formula (I):

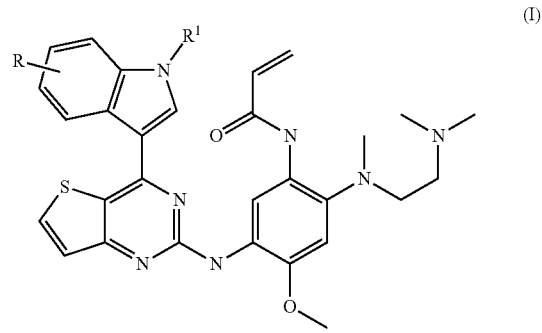

or the general formula (III):

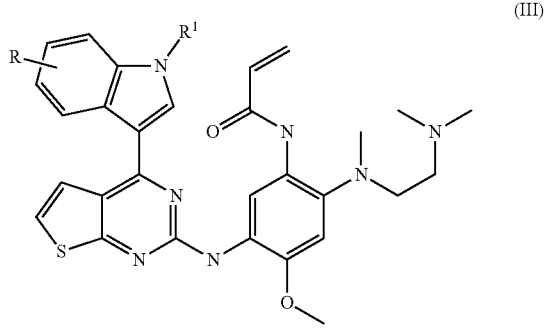

or their respective geometric isomers and a pharmaceutically acceptable salt, prodrugs and solvates thereof, wherein R and $R^1$ is independently H, halogen, SH, OH, $NO_2$, CN, $C_{1-6}$ alkyl, $C_{1-6}$alkoxy, $C_{1-6}$ alkoxycarbonyl, $diC_{1-6}$ alkylamino$C_{2-6}$ alkylcarbonyl, amino, $C_{1-6}$ alkylamino, $diC_{1-6}$ alkylamino, carbamoyl, $C_{1-6}$ alkylcarbamoyl, di($C_{1-6}$ alkyl)carbamoyl, $diC_{1-6}$ alkylamino$C_{2-6}$ alkylcarbamoyl, sulfamoyl, $C_{1-6}$ alkylsulfonyl, $C_{1-6}$ alkylsulfinyl, $diC_{1-6}$ alkylamino$C_{2-6}$ alkylsulfamoyl, $diC_{1-6}$ alkylphsophonyl$C_{1-6}$ alkyl, hydroxy$C_{2-6}$ alkoxy, hydroxycarbonyl$C_{1-6}$ alkyl, $C_{1-6}$ alkoxy$C_{1-6}$ alkyl, $diC_{1-6}$ alkylamino$C_{2-6}$ alkylamino, substituted $diC_{1-6}$ alkylamino$C_{2-6}$ alkylamino, amino$C_{1-6}$ alkyl, $diC_{1-6}$ alkylaminoacetyl, hydroxy$diC_{2-6}$ alkylamino, $C_{1-6}$ alkylamino$C_{2-6}$ alkoxy, $diC_{1-6}$ alkylamino$C_{2-6}$ alkoxy, heteroaryl, heterocycle, heterocyclic oxy, heterocyclicthio, heterocyclicsulfinyl, heterocyclic sulfonyl, heterocyclic sulfamoyl, heterocyclic $C_{1-6}$ alkyl, heterocyclic $C_{1-6}$alkoxy, heterocyclic amino, heterocyclic $C_{1-6}$ alkylamino, heterocyclic carbonyl, or heterocyclic $C_{1-6}$ alkylcarbonyl; wherein a heterocycle is saturated or partially unsaturated 3 to 8 membered cyclic or bicyclic hetero ring with one or more N, O, S, SO, and $SO_2$, in which C or the hetero atom may have one or more substituents selected from the group consisting of $C_{1-6}$ alkyl, hydroxy, hydroxy $C_{1-6}$ alkyl, $C_{1-6}$ alkylcarbonyl, $C_{1-6}$ alkyl amino, and di $C_{1-6}$ alkylamino.

In one embodiment, the present invention further discloses pharmaceutical compositions comprising the above compounds and a pharmaceutically acceptable excipient, and methods of treating cancers using the pharmaceutical compositions of the present invention.

In one embodiment, compounds of the present invention are selected from the group consisting of
N-[2-[2-(dimethylamino)ethyl-methyl-amino]-4-methoxy-5-[[4-(1-methylindol-3-yl)thieno[3,2-d]pyrimidin-2-yl]amino]phenyl]prop-2-enamide,
N-[2-[2-(dimethylamino)ethyl-methyl-amino]-5-[[4-(1-ethylindol-3-yl)thieno[3,2-d]pyrimidin-2-yl]amino]-4-methoxy-phenyl]prop-2-enamide,
N-[2-[2-(dimethylamino)ethyl-methyl-amino]-5-[[4-(1-isopropylindol-3-yl)thieno[3,2-d]pyrimidin-2-yl]amino]-4-methoxy-phenyl]prop-2-enamide,
N-[5-[[4-(1-tert-butylindol-3-yl)thieno[3,2-d]pyrimidin-2-yl]amino]-2-[2-(dimethylamino)ethyl-methyl-amino]-4-methoxy-phenyl]prop-2-enamide,
N-[2-[2-(dimethylamino)ethyl-methyl-amino]-5-[[4-(1,5-dimethylindol-3-yl)thieno[3,2-d]pyrimidin-2-yl]amino]-4-methoxy-phenyl]prop-2-enamide,
N-[2-[2-(dimethylamino)ethyl-methyl-amino]-4-methoxy-5-[[4-(5-methoxy-1-methyl-indol-3-yl)thieno[3,2-d]pyrimidin-2-yl]amino]phenyl]prop-2-enamide,
N-[2-[2-(dimethylamino)ethyl-methyl-amino]-4-methoxy-5-[[4-(6-methoxy-1-methyl-indol-3-yl)thieno[3,2-d]pyrimidin-2-yl]amino]phenyl]prop-2-enamide,
N-[2-[2-(dimethylamino)ethyl-methyl-amino]-5-[[4-(1,6-dimethylindol-3-yl)thieno[3,2-d]pyrimidin-2-yl]amino]-4-methoxy-phenyl]prop-2-enamide, and
N-[2-[2-(dimethylamino)ethyl-methyl-amino]-4-methoxy-5-[[4-(1-methylindol-3-yl)thieno[2,3-d]pyrimidin-2-yl]amino]phenyl]prop-2-enamide.

Also disclosed are methods of using the compounds of the present invention as selective mutant epidermal growth factor receptor tyrosine kinase (EGFR-TK) inhibitor, and for the treatment of EGFR related diseases and disorders such as cancer. A pharmaceutical composition of the present invention can be used for inhibiting the growth of a cancer cell which overexpresses the epidermal growth factor receptor (EGFR), comprising administering an effective amount of a compound of claim 1 to the cell. In one embodiment, the EGFR expressed by the cancer cell is a mutant EGFR. For example, the mutant EGFR is a T709M mutant, an L858R mutant or a delE746-A750 mutant.

The present invention further provides for a method for treating a subject in need thereof, comprising administering to the subject a pharmaceutical composition of the present invention. In one embodiment, the subject is a human suffering from a diseased caused by abnormal cell proliferation, e.g. abnormal cell proliferation is caused by overexpression of EGFR. In one embodiment, the abnormal cell proliferation is caused by overexpression of EGFR selected from the group consisting of ErbB1, ErbB32, ErbB3, and ErbB4. In one embodiment, the subject is suffering from a relapsed or acquired resistant malignant disease. In one embodiment, the subject is a human suffering from NSCLC.

DETAILED DESCRIPTION OF THE INVENTION

In a first embodiment, a compound of the present invention has the formula (I) illustrated below, or its geometric isomers, enantiomers, diastereomers, racemates, pharmaceutically acceptable salts, prodrugs and solvates thereof:

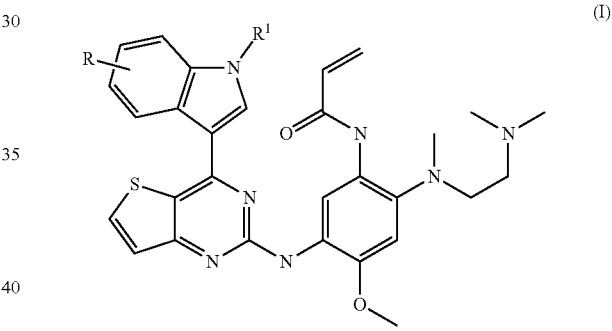

(I)

R and $R^1$ is independently H, halogen, SH, OH, $NO_2$, CN, $C_{1-6}$ alkyl, $C_{1-6}$alkoxy, $C_{1-6}$ alkoxycarbonyl, $diC_{1-6}$ alkylamino$C_{2-6}$ alkylcarbonyl, amino, $C_{1-6}$ alkylamino, $diC_{1-6}$ alkylamino, carbamoyl, $C_{1-6}$ alkylcarbamoyl, di($C_{1-6}$ alkyl)carbamoyl, $diC_{1-6}$ alkylamino$C_{2-6}$ alkylcarbamoyl, sulfamoyl, $C_{1-6}$ alkylsulfonyl, $C_{1-6}$ alkylsulfinyl, $diC_{1-6}$ alkylamino$C_{2-6}$ alkylsulfamoyl, $diC_{1-6}$ alkylphsophonyl$C_{1-6}$ alkyl, hydroxy$C_{2-6}$alkoxy, hydroxycarbonyl$C_{1-6}$ alkyl, $C_{1-6}$ alkoxy$C_{1-6}$ alkyl, $diC_{1-6}$ alkylamino$C_{2-6}$ alkylamino, substituted $diC_{1-6}$ alkylamino$C_{2-6}$ alkylamino, amino$C_{1-6}$ alkyl, $diC_{1-6}$ alkylaminoacetyl, hydroxy$diC_{2-6}$ alkylamino, $C_{1-6}$ alkylamino$C_{2-6}$ alkoxy, $diC_{1-6}$ alkylamino$C_{2-6}$ alkoxy, heteroaryl, heterocycle, heterocyclic oxy, heterocyclicthio, heterocyclicsulfinyl, heterocyclic sulfonyl, heterocyclic sulfamoyl, heterocyclic $C_{1-6}$ alkyl, heterocyclic $C_{1-6}$alkoxy, heterocyclic amino, heterocyclic $C_{1-6}$ alkylamino, heterocyclic carbonyl, or heterocyclic $C_{1-6}$ alkylcarbonyl; wherein a heterocycle is saturated or partially unsaturated 3 to 8 membered cyclic or bicyclic hetero ring with one or more N, O, S, SO, and $SO_2$, in which C or the hetero atom may have one or more substituents selected from the group consisting of $C_{1-6}$ alkyl, hydroxy, hydroxy $C_{1-6}$ alkyl, $C_{1-6}$ alkylcarbonyl, $C_{1-6}$ alkyl amino, and di $C_{1-6}$ alkylamino.

In a second embodiment, the compound has the formula (II) illustrated below, or its geometric isomers, enantiomers, diastereomers, racemates, pharmaceutically acceptable salts, prodrugs and solvates thereof:

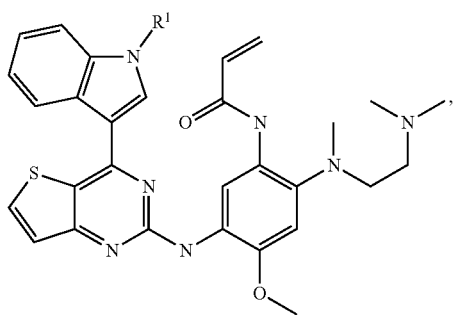
(II)

wherein R¹ is as previously defined.

In a third embodiment, the compound has the formula (III) illustrated below, or its geometric isomers, enantiomers, diastereomers, racemates, pharmaceutically acceptable salts, prodrugs and solvates thereof:

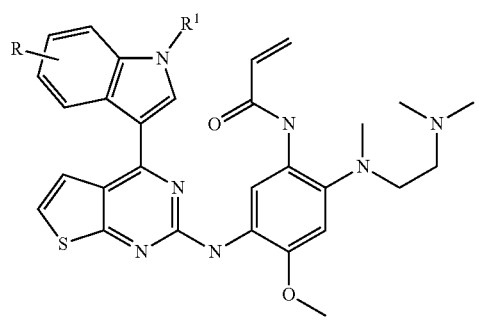
(III)

wherein R and R¹ are as previously defined.

In a fourth embodiment, the compound has the formula (IV) illustrated below, or its geometric isomers, enantiomers, diastereomers, racemates, pharmaceutically acceptable salts, prodrugs and solvates thereof:

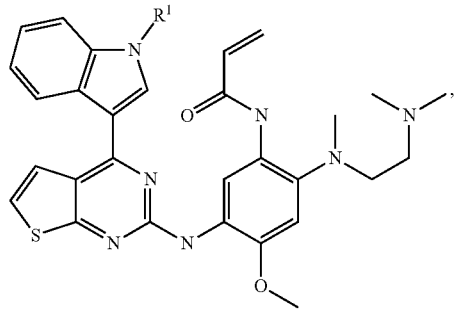
(IV)

wherein R¹ is as previously defined.

Representative compounds of the present invention also include, but are not limited to the compounds listed in Table I below or its geometric isomers, enantiomers, diastereomers, racemates, pharmaceutically acceptable salts, prodrugs and solvates thereof:

TABLE 1

| Compound # | Structure |
|---|---|
| 1 | N-[2-[2-(dimethylamino)ethyl-methyl-amino]-4-methoxy-5-[[4-(1-methylindol-3-yl)thieno[3,2-d]pyrimidin-2-yl]amino]phenyl]prop-2-enamide |
| 2 | N-[2-[2-(dimethylamino)ethyl-methyl-amino]-5-[[4-(1-ethylindol-3-yl)thieno[3,2-d]pyrimidin-2-yl]amino]-4-methoxy-phenyl]prop-2-enamide |
| 3 | N-[2-[2-(dimethylamino)ethyl-methyl-amino]-5-[[4-(1-isopropylindol-3-yl)thieno[3,3-d]pyrimidin-2-yl]amino]-4-methoxy-phenyl]prop-2-enamide |

TABLE 1-continued

| Compound # | Structure |
|---|---|
| 4 | N-[5-[[4-(1-tert-butylindol-3-yl)thieno[3,2-d]pyrimidin-2-yl]amino]-2-[2-(dimethylamino)ethyl-methyl-amino]-4-methoxy-phenyl]prop-2-enamide |
| 5 | N-[2-[2-(dimethylamino)ethyl-methyl-amino]-5-[[4-(1,5-dimethylindol-3-yl)thienol[3,2-d]pyrimidin-2-yl]amino]-4-methoxy-phenyl]prop-2-enamide |
| 6 | N-[2-[2-(dimethylamino)ethyl-methyl-amino]-4-methoxy-5-[[4-(5-methoxy-1-methyl-indol-3-yl)thieno[3,2-d]pyrimidin-2-yl]amino]phenyl]prop-2-enamide |
| 7 | N-[2-[2-(dimethylamino)ethyl-methyl-amino]-4-methoxy-5-[[4-(6-methoxy-1-methyl-indol-3-yl)thieno[3,2-d]pyrimidin-2-yl]amino]phenyl]prop-2-enamide |
| 8 | N-[2-[2-(dimethylamino)ethyl-methyl-amino]-5-[[4-(1,6-dimethylindol-3-yl)thieno[3,2-d]pyrimidin-2-yl]amino]-4-methoxy-phenyl]prop-2-enamide |
| 9 | N-[2-[2-(dimethylamino)ethyl-methyl-amino]-4-methoxy-5-[[4-(1-methylindol-3-yl)thieno[2,3-d]pyrimidin-2-yl]amino]phenyl]prop-2-enamide |

The invention provides methods for the prevention or treatment of diseases or conditions involving aberrant proliferation, differentiation or survival of cells. In one embodiment, the invention further provides for the use of one or more compounds of the invention in the manufacture of a medicament for halting or decreasing diseases involving aberrant proliferation, differentiation, or survival of cells. In preferred embodiments, the disease is cancer. In one embodiment, the invention relates to a method of treating cancer in a subject in need of treatment comprising administering to said subject a therapeutically effective amount of a compound of the invention.

In comparison with other known EGFR inhibitors the compounds of the invention show better activity/efficacy, and/or favorable toxicity profiles, and/or better physical properties, such as aqueous solubility, permeability profiles, and protein binding, and/or favorable metabolic profiles. Accordingly, the compounds of the invention are useful in the treatment of diseases involved EGFR and/or activating mutations of EGFR and/or resistance mutations of EGFR.

Compounds and compositions described herein are generally useful for the inhibition of mutant of EGFR as compared to WT EGFR. In some examples, the mutant of EGFR is T790M, and other mutants of EGFR are L858R or T790M. In another example, it may be a deletion mutation of EGFR, delE746-A750, an activating mutation of EGFR.

The activity of a compound in this invention as a selective inhibitor may be assayed in vitro, in a cell line or in vivo. In vitro assays determine inhibition of the phosphorylation activity and subsequent functional results, or ATPase activity of activated EGFR.

The term "cancer" refers to any cancer caused by the proliferation of malignant neoplastic cells, such as tumors, neoplasms, carcinomas, sarcomas, leukemias, lymphomas and the like. For example, cancers include, but are not limited to, mesothelioma, leukemias and lymphomas such as cutaneous T-cell lymphomas (CTCL), noncutaneous peripheral T-cell lymphomas, lymphomas associated with human T-cell lymphotrophic virus (HTLV) such as adult T-cell leukemia/lymphoma (ATLL), B-cell lymphoma, acute non-lymphocytic leukemias, chronic lymphocytic leukemia, chronic myelogenous leukemia, acute myelogenous leukemia, lymphomas, and multiple myeloma, non-Hodgkin lymphoma, acute lymphatic leukemia (ALL), chronic lymphatic leukemia (CLL), Hodgkin's lymphoma, Burkitt lymphoma, adult T-cell leukemia lymphoma, acute-myeloid leukemia (AML), chronic myeloid leukemia (CML), or hepatocellular carcinoma. Further examples include myelodisplastic syndrome, childhood solid tumors such as brain tumors, neuroblastoma, retinoblastoma, Wilms' tumor, bone tumors, and soft-tissue sarcomas, common solid tumors of adults such as head and neck cancers (e.g., oral, laryngeal, nasopharyngeal and esophageal), genitourinary cancers (e.g., prostate, bladder, renal, uterine, ovarian, testicular), lung cancer (e.g., small-cell and non-small cell), breast cancer, pancreatic cancer, melanoma and other skin cancers, stomach cancer, brain tumors, tumors related to Gorlin's syndrome (e.g., medulloblastoma, meningioma, etc.), and liver cancer. Additional exemplary forms of cancer which may be treated by the subject compounds include, but are not limited to, cancer of skeletal or smooth muscle, stomach cancer, cancer of the small intestine, rectum carcinoma, cancer of the salivary gland, endometrial cancer, adrenal cancer, anal cancer, rectal cancer, parathyroid cancer, and pituitary cancer.

Additional cancers that the compounds described herein may be useful in preventing, treating and studying are, for example, colon carcinoma, familiary adenomatous polyposis carcinoma and hereditary non-polyposis colorectal cancer, or melanoma. Further, cancers include, but are not limited to, labial carcinoma, larynx carcinoma, hypopharynx carcinoma, tongue carcinoma, salivary gland carcinoma, gastric carcinoma, adenocarcinoma, thyroid cancer (medullary and papillary thyroid carcinoma), renal carcinoma, kidney parenchyma carcinoma, cervix carcinoma, uterine corpus carcinoma, endometrium carcinoma, chorion carcinoma, testis carcinoma, urinary carcinoma, melanoma, brain tumors such as glioblastoma, astrocytoma, meningioma, medulloblastoma and peripheral neuroectodermal tumors, gall bladder carcinoma, bronchial carcinoma, multiple myeloma, basalioma, teratoma, retinoblastoma, choroidea melanoma, seminoma, rhabdomyosarcoma, craniopharyngeoma, osteosarcoma, chondrosarcoma, myosarcoma, liposarcoma, fibrosarcoma, Ewing sarcoma, and plasmocytoma. In one aspect of the invention, the present invention provides for the use of one or more compounds of the invention in the manufacture of a medicament for the treatment of cancer.

In one embodiment, the present invention includes the use of one or more compounds of the invention in the manufacture of a medicament that prevents further aberrant proliferation, differentiation, or survival of cells. For example, compounds of the invention may be useful in preventing tumors from increasing in size or from reaching a metastatic state. The subject compounds may be administered to halt the progression or advancement of cancer or to induce tumor apoptosis or to inhibit tumor angiogenesis. In addition, the instant invention includes use of the subject compounds to prevent a recurrence of cancer.

This invention further embraces the treatment or prevention of cell proliferative disorders such as hyperplasias, dysplasias and pre-cancerous lesions. Dysplasia is the earliest form of pre-cancerous lesion recognizable in a biopsy by a pathologist. The subject compounds may be administered for the purpose of preventing said hyperplasias, dysplasias or pre-cancerous lesions from continuing to expand or from becoming cancerous. Examples of pre-cancerous lesions may occur in skin, esophageal tissue, breast and cervical intra-epithelial tissue.

"Combination therapy" includes the administration of the subject compounds in further combination with other biologically active ingredients (such as, but not limited to, a second and different antineoplastic agent) and non-drug therapies (such as, but not limited to, surgery or radiation treatment). For instance, the compounds of the invention can be used in combination with other pharmaceutically active compounds, preferably compounds that are able to enhance the effect of the compounds of the invention. The compounds of the invention can be administered simultaneously (as a single preparation or separate preparation) or sequentially to the other drug therapy. In general, a combination therapy envisions administration of two or more drugs during a single cycle or course of therapy.

"Combination therapy" includes the administration of the subject compounds in further combination with other biologically active ingredients (such as, but not limited to, a second and different antineoplastic agent) and non-drug therapies (such as, but not limited to, surgery or radiation treatment). For instance, the compounds of the invention can be used in combination with other pharmaceutically active compounds, preferably compounds that are able to enhance the effect of the compounds of the invention. The compounds of the invention can be administered simultaneously (as a single preparation or separate preparation) or sequentially to the other drug therapy. In general, a combination therapy envisions administration of two or more drugs during a single cycle or course of therapy.

In one aspect of the invention, the subject compounds may be administered in combination with one or more separate agents that modulate protein kinases involved in various disease states. Examples of such kinases may include, but are not limited to: serine/threonine specific kinases, receptor tyrosine specific kinases and non-receptor tyrosine specific kinases. Serine/threonine kinases include mitogen activated protein kinases (MAPK), meiosis specific kinase (Aurora), RAF and Aurora kinase. Examples of receptor kinase families include epidermal growth factor receptor (EGFR) (e.g. HER2/neu, HER3, HER4, ErbB, ErbB2, ErbB3, ErbB4, Xmrk, DER, Let23); fibroblast growth factor (FGF) receptor (e.g. FGF-R1, GFF-R2/BEK/CEK3, FGF-R3/CEK2, FGF-R4/TKF, KGF-R); hepatocyte growth/scatter factor receptor (HGFR) (e.g, MET, RON, SEA, SEX); insulin receptor (e.g. IGFI-R); Eph (e.g. CEK5, CEK8, EBK, ECK, EEK, EHK-1, EHK-2, ELK, EPH, ERK, HEK, MDK2, MDK5, SEK); Axl (e.g. Mer/Nyk, Rse); RET; and platelet-derived growth factor receptor (PDGFR) (e.g. PDGFα-R, PDGFβ-R, CSF1-R/FMS, SCF-R/C-KIT, VEGF-R/FLT, NEK/FLKL, FLT3/FLK2/STK-1). Non-receptor tyrosine kinase families include, but are not limited to, BCR-ABL (e.g. $p43^{abl}$, ARG); BTK (e.g. ITK/EMT, TEC); CSK, FAK, FPS, JAK, SRC, BMX, FER, CDK and SYK.

In a preferred embodiment, subject compounds may be combined with antineoplastic agents (e.g. small molecules, monoclonal antibodies, antisense RNA, and fusion proteins) that inhibit one or more biological targets such as Zolinza, Tykerb, Gleevec, Sutent, Sprycel, Nexavar, Sorafinib, CNF2024, RG108, BMS387032, Affinitak, Avastin, Herceptin, Erbitux, AG24322, PD325901, ZD6474, PD184322, Obatodax, ABT737 and AEE788. Such combinations may enhance therapeutic efficacy over efficacy achieved by any of the agents alone and may prevent or delay the appearance of resistant mutational variants.

In certain preferred embodiments, the compounds of the invention are administered in combination with a chemotherapeutic agent. Chemotherapeutic agents encompass a wide range of therapeutic treatments in the field of oncology. These agents are administered at various stages of the disease for the purposes of shrinking tumors, destroying remaining cancer cells left over after surgery, inducing remission, maintaining remission and/or alleviating symptoms relating to the cancer or its treatment. Examples of such agents include, but are not limited to, alkylating agents such as mustard gas derivatives (Mechlorethamine, cylophosphamide, chlorambucil, melphalan, ifosfamide), ethylenimines (thiotepa, hexamethylmelanine), Alkylsulfonates (Busulfan), Hydrazines and Triazines (Altretamine, Procarbazine, Dacarbazine and Temozolomide), Nitrosoureas (Carmustine, Lomustine and Streptozocin), Ifosfamide and metal salts (Carboplatin, Cisplatin, and Oxaliplatin); plant alkaloids such as Podophyllotoxins (Etoposide and Tenisopide), Taxanes (Paclitaxel and Docetaxel), Vinca alkaloids (Vincristine, Vinblastine, Vindesine and Vinorelbine), and Camptothecan analogs (Irinotecan and Topotecan); anti-tumor antibiotics such as Chromomycins (Dactinomycin and Plicamycin), Anthracyclines (Doxorubicin, Daunorubicin, Epirubicin, Mitoxantrone, Valrubicin and Idarubicin), and miscellaneous antibiotics such as Mitomycin, Actinomycin and Bleomycin; anti-metabolites such as folic acid antagonists (Methotrexate, Pemetrexed, Raltitrexed, Aminopterin), pyrimidine antagonists (5-Fluorouracil, Floxuridine, Cytarabine, Capecitabine, and Gemcitabine), purine antagonists (6-Mercaptopurine and 6-Thioguanine) and adenosine deaminase inhibitors (Cladribine, Fludarabine, Mercaptopurine, Clofarabine, Thioguanine, Nelarabine and Pentostatin); topoisomerase inhibitors such as topoisomerase I inhibitors (Ironotecan, topotecan) and topoisomerase II inhibitors (Amsacrine, etoposide, etoposide phosphate, teniposide); monoclonal antibodies (Alemtuzumab, Gemtuzumab ozogamicin, Rituximab, Trastuzumab, Ibritumomab Tioxetan, Cetuximab, Panitumumab, Tositumomab, Bevacizumab); and miscellaneous anti-neoplastics such as ribonucleotide reductase inhibitors (Hydroxyurea); adrenocortical steroid inhibitor (Mitotane); enzymes (Asparaginase and Pegaspargase); anti-microtubule agents (Estramustine); and retinoids (Bexarotene, Isotretinoin, Tretinoin (ATRA).

In certain preferred embodiments, the compounds of the invention are administered in combination with a chemoprotective agent. Chemoprotective agents act to protect the body or minimize the side effects of chemotherapy. Examples of such agents include, but are not limited to, amfostine, mesna, and dexrazoxane.

In one aspect of the invention, the subject compounds are administered in combination with radiation therapy. Radiation is commonly delivered internally (implantation of radioactive material near cancer site) or externally from a machine that employs photon (x-ray or gamma-ray) or particle radiation. Where the combination therapy further comprises radiation treatment, the radiation treatment may be conducted at any suitable time so long as a beneficial effect from the co-action of the combination of the therapeutic agents and radiation treatment is achieved. For example, in appropriate cases, the beneficial effect is still achieved when the radiation treatment is temporally removed from the administration of the therapeutic agents, perhaps by days or even weeks.

It will be appreciated that compounds of the invention can be used in combination with an immunotherapeutic agent. One form of immunotherapy is the generation of an active systemic tumor-specific immune response of host origin by administering a vaccine composition at a site distant from the tumor. Various types of vaccines have been proposed, including isolated tumor-antigen vaccines and anti-idiotype vaccines. Another approach is to use tumor cells from the subject to be treated, or a derivative of such cells (reviewed by Schirrmacher et al. (1995) J. Cancer Res. Clin. Oncol. 121:487). In U.S. Pat. No. 5,484,596, Hanna Jr. et al. claims a method for treating a resectable carcinoma to prevent recurrence or metastases, comprising surgically removing the tumor, dispersing the cells with collagenase, irradiating the cells, and vaccinating the patient with at least three consecutive doses of about $10^7$ cells.

In one embodiment, compounds of the invention can be used to induce or inhibit apoptosis, a physiological cell death process critical for normal development and homeostasis. Alterations of apoptotic pathways contribute to the pathogenesis of a variety of human diseases. Compounds of the invention, as modulators of apoptosis, will be useful in the treatment of a variety of human diseases with aberrations in apoptosis including cancer (particularly, but not limited to, follicular lymphomas, carcinomas with p53 mutations, hormone dependent tumors of the breast, prostate and ovary, and precancerous lesions such as familial adenomatous polyposis), viral infections (including, but not limited to, herpes virus, poxvirus, Epstein-Barr virus, Sindbis virus and adenovirus), autoimmune diseases (including, but not limited to, systemic lupus, erythematosus, immune mediated glomerulonephritis, rheumatoid arthritis, psoriasis, inflammatory bowel diseases, and autoimmune diabetes mellitus), hematological diseases (including, but not limited to, chronic anemia and aplastic anemia), and cancer pain.

The invention encompasses pharmaceutical compositions comprising pharmaceutically acceptable salts of the compounds of the invention as described above. The invention also encompasses pharmaceutical compositions comprising hydrates of the compounds of the invention. The term "hydrate" includes but is not limited to hemihydrate, monohydrate, dihydrate, trihydrate and the like. The invention further encompasses pharmaceutical compositions comprising any solid or liquid physical form of the compound of the invention. For example, the compounds can be in a crystalline form, in amorphous form, and have any particle size. The particles may be micronized, or may be agglomerated, particulate granules, powders, oils, oily suspensions or any other form of solid or liquid physical form.

The compounds of the invention, and derivatives, fragments, analogs, homologs, pharmaceutically acceptable salts or hydrate thereof can be incorporated into pharmaceutical compositions suitable for administration, together with a pharmaceutically acceptable carrier or excipient. Such compositions typically comprise a therapeutically effective amount of any of the compounds above, and a pharmaceutically acceptable carrier. Preferably, the effective amount when treating cancer is an amount effective to selectively induce terminal differentiation of suitable neoplastic cells and less than an amount which causes toxicity in a patient.

Compounds of the invention may be administered by any suitable means, including, without limitation, parenteral, intravenous, intramuscular, subcutaneous, implantation, oral, sublingual, buccal, nasal, pulmonary, transdermal, topical, vaginal, rectal, and transmucosal administrations or the like. Topical administration can also involve the use of transdermal administration such as transdermal patches or iontophoresis devices. Pharmaceutical preparations include a solid, semisolid or liquid preparation (tablet, pellet, troche, capsule, suppository, cream, ointment, aerosol, powder, liquid, emulsion, suspension, syrup, injection etc.) containing a compound of the invention as an active ingredient, which is suitable for selected mode of administration. In one embodiment, the pharmaceutical compositions are administered orally, and are thus formulated in a form suitable for oral administration, i.e., as a solid or a liquid preparation. Suitable solid oral formulations include tablets, capsules, pills, granules, pellets, sachets and effervescent, powders, and the like. Suitable liquid oral formulations include solutions, suspensions, dispersions, emulsions, oils and the like. In one embodiment of the present invention, the composition is formulated in a capsule. In accordance with this embodiment, the compositions of the present invention comprise in addition to the active compound and the inert carrier or diluent, a hard gelatin capsule.

Any inert excipient that is commonly used as a carrier or diluent may be used in the formulations of the present invention, such as for example, a gum, a starch, a sugar, a cellulosic material, an acrylate, or mixtures thereof. A preferred diluent is microcrystalline cellulose. The compositions may further comprise a disintegrating agent (e.g., croscarmellose sodium) and a lubricant (e.g., magnesium stearate), and may additionally comprise one or more additives selected from a binder, a buffer, a protease inhibitor, a surfactant, a solubilizing agent, a plasticizer, an emulsifier, a stabilizing agent, a viscosity increasing agent, a sweetener, a film forming agent, or any combination thereof. Furthermore, the compositions of the present invention may be in the form of controlled release or immediate release formulations.

For liquid formulations, pharmaceutically acceptable carriers may be aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of petroleum, animal, vegetable, or synthetic origin, for example, peanut oil, soybean oil, mineral oil, olive oil, sunflower oil, and fish-liver oil. Solutions or suspensions can also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide.

It is especially advantageous to formulate oral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

Daily administration may be repeated continuously for a period of several days to several years. Oral treatment may continue for between one week and the life of the patient. Preferably the administration may take place for five consecutive days after which time the patient can be evaluated to determine if further administration is required. The administration can be continuous or intermittent, e.g., treatment for a number of consecutive days followed by a rest period. The compounds of the present invention may be administered intravenously on the first day of treatment, with oral administration on the second day and all consecutive days thereafter.

The preparation of pharmaceutical compositions that contain an active component is well understood in the art, for example, by mixing, granulating, or tablet-forming processes. The active therapeutic ingredient is often mixed with excipients that are pharmaceutically acceptable and compatible with the active ingredient. For oral administration, the active agents are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions and the like as detailed above.

The amount of the compound administered to the patient is less than an amount that would cause toxicity in the patient. In certain embodiments, the amount of the compound that is administered to the patient is less than the amount that causes a concentration of the compound in the patient's plasma to equal or exceed the toxic level of the compound. The optimal amount of the compound that should be administered to the patient in the practice of the present invention will depend on the particular compound used and the type of cancer being treated.

Various terms used to describe this invention throughout this specification and claims have the following meanings unless otherwise limited in specific instances.

An "aliphatic group" or "aliphatic" is non-aromatic moiety that may be saturated (e.g. single bond) or contain one or more units of unsaturation, (e.g., double and/or triple bonds). An aliphatic group may be straight chained, branched or cyclic, contain carbon, hydrogen or, optionally, one or more heteroatoms and may be substituted or unsubstituted. An aliphatic group preferably contains between about 1 and about 24 atoms, more preferably between about 4 to about 24 atoms, more preferably between about 4-12 atoms, more typically between about 4 and about 8 atoms.

The term "alkyl" embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about eight carbon atoms. Examples of such radicals include methyl, ethyl, n-propyl, isopropyl, n-butyl, isobutyl, sec-butyl, tert-butyl, pentyl, iso-amyl, hexyl and the like.

The term "alkenyl" embraces linear or branched radicals having at least one carbon-carbon double bond of two to about twenty carbon atoms or, preferably, two to about twelve carbon atoms. More preferred alkenyl radicals are "lower alkenyl" radicals having two to about ten carbon atoms and more preferably about two to about eight carbon atoms. Examples of alkenyl radicals include ethenyl, allyl, propenyl, butenyl and 4-methylbutenyl. The terms "alkenyl", and "lower alkenyl", embrace radicals having "cis" and "trans" orientations, or alternatively, "E" and "Z" orientations.

The term "alkynyl" embraces linear or branched radicals having at least one carbon-carbon triple bond of two to about twenty carbon atoms or, preferably, two to about twelve carbon atoms. More preferred alkynyl radicals are "lower alkynyl" radicals having two to about ten carbon atoms and more preferably about two to about eight carbon atoms. Examples of alkynyl radicals include propargyl, 1-propynyl, 2-propynyl, 1-butyne, 2-butynyl and 1-pentynyl.

The term "cycloalkyl" embraces saturated carbocyclic radicals having three to about twelve carbon atoms. The term "cycloalkyl" embraces saturated carbocyclic radicals having three to about twelve carbon atoms. More preferred cycloalkyl radicals are "lower cycloalkyl" radicals having three to about eight carbon atoms. Examples of such radicals include cyclopropyl, cyclobutyl, cyclopentyl and cyclohexyl.

The term "cycloalkenyl" embraces partially unsaturated carbocyclic radicals having three to twelve carbon atoms. Cycloalkenyl radicals that are partially unsaturated carbocyclic radicals that contain two double bonds (that may or may not be conjugated) can be called "cycloalkyldienyl". More preferred cycloalkenyl radicals are "lower cycloalkenyl" radicals having four to about eight carbon atoms. Examples of such radicals include cyclobutenyl, cyclopentenyl and cyclohexenyl.

The term "alkoxy" embraces linear or branched oxy-containing radicals each having alkyl portions of one to about twenty carbon atoms or, preferably, one to about twelve carbon atoms. More preferred alkoxy radicals are "lower alkoxy" radicals having one to about ten carbon atoms and more preferably having one to about eight carbon atoms. Examples of such radicals include methoxy, ethoxy, propoxy, butoxy and tert-butoxy.

The term "alkoxyalkyl" embraces alkyl radicals having one or more alkoxy radicals attached to the alkyl radical, that is, to form monoalkoxyalkyl and dialkoxyalkyl radicals.

The term "aryl", alone or in combination, means a carbocyclic aromatic system containing one, two or three rings wherein such rings may be attached together in a pendent manner or may be fused. The term "aryl" embraces aromatic radicals such as phenyl, naphthyl, tetrahydronaphthyl, indane and biphenyl.

The terms "heterocyclyl", "heterocycle" "heterocyclic" or "heterocyclo" embrace saturated, partially unsaturated and unsaturated heteroatom-containing ring-shaped radicals, which can also be called "heterocyclyl", "heterocycloalkenyl" and "heteroaryl" correspondingly, where the heteroatoms may be selected from nitrogen, sulfur and oxygen. Examples of saturated heterocyclyl radicals include saturated 3 to 6-membered heteromonocyclic group containing 1 to 4 nitrogen atoms (e.g. pyrrolidinyl, imidazolidinyl, piperidino, piperazinyl, etc.); saturated 3 to 6-membered heteromonocyclic group containing 1 to 2 oxygen atoms and 1 to 3 nitrogen atoms (e.g. morpholinyl, etc.); saturated 3 to 6-membered heteromonocyclic group containing 1 to 2 sulfur atoms and 1 to 3 nitrogen atoms (e.g., thiazolidinyl, etc.). Examples of partially unsaturated heterocyclyl radicals include dihydrothiophene, dihydropyran, dihydrofuran and dihydrothiazole. Heterocyclyl radicals may include a pentavalent nitrogen, such as in tetrazolium and pyridinium radicals. The term "heterocycle" also embraces radicals where heterocyclyl radicals are fused with aryl or cycloalkyl radicals. Examples of such fused bicyclic radicals include benzofuran, benzothiophene, and the like.

The term "heteroaryl" embraces unsaturated heterocyclyl radicals. Examples of heteroaryl radicals include unsaturated 3 to 6 membered heteromonocyclic group containing 1 to 4 nitrogen atoms, for example, pyrrolyl, pyrrolinyl, imidazolyl, pyrazolyl, pyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.) tetrazolyl (e.g. 1H-tetrazolyl, 2H-tetrazolyl, etc.), etc.; unsaturated condensed heterocyclyl group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl, etc.; unsaturated 3 to 6-membered heteromonocyclic group containing an oxygen atom; unsaturated 3 to 6-membered heteromonocyclic group containing a sulfur atom; unsaturated 3- to 6-membered heteromonocyclic group containing 1 to 2 oxygen atoms and 1 to 3 nitrogen atoms, etc.; unsaturated condensed heterocyclyl group containing 1 to 2 oxygen atoms and 1 to 3 nitrogen atoms; unsaturated 3 to 6-membered heteromonocyclic group containing 1 to 2 sulfur atoms and 1 to 3 nitrogen atoms, for example, thiazolyl, thiadiazolyl, etc.; unsaturated condensed heterocyclyl group containing 1 to 2 sulfur atoms and 1 to 3 nitrogen atoms and the like.

The term "heterocycloalkyl" embraces heterocyclo-substituted alkyl radicals. More preferred heterocycloalkyl radicals are "lower heterocycloalkyl" radicals having one to six carbon atoms in the heterocyclo radicals.

The terms "aralkyl" or "arylalkyl" embrace aryl-substituted alkyl radicals such as benzyl, diphenylmethyl, triphenylmethyl, phenylethyl, and diphenylethyl.

The term "aryloxy" embraces aryl radicals attached through an oxygen atom to other radicals.

The terms "aralkoxy" or "arylalkoxy" embrace aralkyl radicals attached through an oxygen atom to other radicals.

The term "aminoalkyl" embraces alkyl radicals substituted with amino radicals. Preferred aminoalkyl radicals have alkyl radicals having about one to about twenty carbon atoms or, preferably, one to about twelve carbon atoms. More preferred aminoalkyl radicals are "lower aminoalkyl" that have alkyl radicals having one to about ten carbon atoms. Most preferred are aminoalkyl radicals having lower alkyl radicals having one to eight carbon atoms. Examples of such radicals include aminomethyl, aminoethyl, and the like.

The term "alkylamino" denotes amino groups which are substituted with one or two alkyl radicals. Preferred alkylamino radicals have alkyl radicals having about one to about twenty carbon atoms or, preferably, one to about twelve carbon atoms. More preferred alkylamino radicals are "lower alkylamino" that have alkyl radicals having one to about ten carbon atoms. Most preferred are alkylamino radicals having lower alkyl radicals having one to about eight carbon atoms. Suitable lower alkylamino may be monosubstituted N-alkylamino or disubstituted N,N-alkylamino, such as N-methylamino, N-ethylamino, N,N-dimethylamino, N,N-diethylamino or the like.

For simplicity, chemical moieties are defined and referred to throughout can be univalent chemical moieties (e.g., alkyl, aryl, etc.) or multivalent moieties under the appropriate structural circumstances clear to those skilled in the art. For example, an "alkyl" moiety can be referred to a monovalent radical (e.g. $CH_3$—$CH_2$—), or in other instances, a bivalent linking moiety can be "alkyl," in which case those skilled in the art will understand the alkyl to be a divalent radical (e.g., —CH$_2$—CH$_2$—), which is equivalent to the term "alkylene." Similarly, in circumstances in which divalent moieties are required and are stated as being "alkoxy", "alkylamino", "aryloxy", "alkylthio", "aryl", "heteroaryl", "heterocyclic", "alkyl", "alkenyl", "alkynyl", "aliphatic", or "cycloalkyl", those skilled in the art will understand that the terms alkoxy", "alkylamino", "aryloxy", "alkylthio", "aryl", "heteroaryl", "heterocyclic", "alkyl", "alkenyl", "alkynyl", "aliphatic", or "cycloalkyl" refer to the corresponding divalent moiety.

The terms "halogen" or "halo" as used herein, refers to an atom selected from fluorine, chlorine, bromine and iodine.

As used herein, the term "aberrant proliferation" refers to abnormal cell growth.

The phrase "adjunctive therapy" encompasses treatment of a subject with agents that reduce or avoid side effects associated with the combination therapy of the present invention, including, but not limited to, those agents, for example, that reduce the toxic effect of anticancer drugs, e.g., bone resorption inhibitors, cardioprotective agents; prevent or reduce the incidence of nausea and vomiting associated with chemotherapy, radiotherapy or operation; or reduce the incidence of infection associated with the administration of myelosuppressive anticancer drugs.

The term "apoptosis" as used herein refers to programmed cell death as signaled by the nuclei in normally functioning human and animal cells when age or state of cell health and condition dictates. An "apoptosis inducing agent" triggers the process of programmed cell death.

The term "cancer" as used herein denotes a class of diseases or disorders characterized by uncontrolled division of cells and the ability of these cells to invade other tissues, either by direct growth into adjacent tissue through invasion or by implantation into distant sites by metastasis.

The term "compound" is defined herein to include pharmaceutically acceptable salts, solvates, hydrates, polymorphs, enantiomers, diastereoisomers, racemates and the like of the compounds having a formula as set forth herein.

The term "devices" refers to any appliance, usually mechanical or electrical, designed to perform a particular function.

As used herein, the term "effective amount of the subject compounds," with respect to the subject method of treatment, refers to an amount of the subject compound which, when delivered as part of desired dose regimen, brings about, e.g. a change in the rate of cell proliferation and/or state of differentiation and/or rate of survival of a cell to clinically acceptable standards. This amount may further relieve to some extent one or more of the symptoms of a neoplasia disorder, including, but is not limited to: 1) reduction in the number of cancer cells; 2) reduction in tumor size; 3) inhibition (i.e., slowing to some extent, preferably stopping) of cancer cell infiltration into peripheral organs; 4) inhibition (i.e., slowing to some extent, preferably stopping) of tumor metastasis; 5) inhibition, to some extent, of tumor growth; 6) relieving or reducing to some extent one or more of the symptoms associated with the disorder; and/or 7) relieving or reducing the side effects associated with the administration of anticancer agents.

The term "hyperplasia," as used herein, refers to excessive cell division or growth.

The phrase an "immunotherapeutic agent" refers to agents used to transfer the immunity of an immune donor, e.g., another person or an animal, to a host by inoculation. The term embraces the use of serum or gamma globulin containing performed antibodies produced by another individual or an animal; nonspecific systemic stimulation; adjuvants; active specific immunotherapy; and adoptive immunotherapy. Adoptive immunotherapy refers to the treatment of a disease by therapy or agents that include host inoculation of sensitized lymphocytes, transfer factor, immune RNA, or antibodies in serum or gamma globulin.

The term "inhibition," in the context of neoplasia, tumor growth or tumor cell growth, may be assessed by delayed appearance of primary or secondary tumors, slowed development of primary or secondary tumors, decreased occurrence of primary or secondary tumors, slowed or decreased severity of secondary effects of disease, arrested tumor growth and regression of tumors, among others. In the extreme, complete inhibition, is referred to herein as prevention or chemoprevention.

The term "metastasis," as used herein, refers to the migration of cancer cells from the original tumor site through the blood and lymph vessels to produce cancers in other tissues. Metastasis also is the term used for a secondary cancer growing at a distant site.

The term "neoplasm," as used herein, refers to an abnormal mass of tissue that results from excessive cell division. Neoplasms may be benign (not cancerous), or malignant (cancerous) and may also be called a tumor. The term "neoplasia" is the pathological process that results in tumor formation.

As used herein, the term "pre-cancerous" refers to a condition that is not malignant, but is likely to become malignant if left untreated.

The term "proliferation" refers to cells undergoing mitosis.

The phrase a "radio therapeutic agent" refers to the use of electromagnetic or particulate radiation in the treatment of neoplasia.

The term "recurrence" as used herein refers to the return of cancer after a period of remission. This may be due to incomplete removal of cells from the initial cancer and may occur locally (the same site of initial cancer), regionally (in vicinity of initial cancer, possibly in the lymph nodes or tissue), and/or distally as a result of metastasis.

The term "treatment" refers to any process, action, application, therapy, or the like, wherein a mammal, including a human being, is subject to medical aid with the object of improving the mammal's condition, directly or indirectly.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid or inorganic acid. Examples of pharmaceutically acceptable nontoxic acid addition salts include, but are not limited to, salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid lactobionic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, "pharmaceutically acceptable carrier" is intended to include any and all solvents, dispersion media, coatings, antibacterial and antifungal agents, isotonic and absorption delaying agents, and the like, compatible with pharmaceutical administration, such as sterile pyrogen-free water. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

As used herein, the term "pre-cancerous" refers to a condition that is not malignant, but is likely to become malignant if left untreated.

The term "subject" as used herein refers to an animal. Preferably the animal is a mammal. More preferably the mammal is a human. A subject also refers to, for example, dogs, cats, horses, cows, pigs, guinea pigs, fish, birds and the like.

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and P. G. M. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

Pharmaceutical Compositions

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a non-toxic, inert solid, semi-solid or liquid filler, diluent, encapsulating material or formulation auxiliary of any type.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethycellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

For pulmonary delivery, a therapeutic composition of the invention is formulated and administered to the patient in solid or liquid particulate form by direct administration e.g., inhalation into the respiratory system. Solid or liquid particulate forms of the active compound prepared for practicing the present invention include particles of respirable size: that is, particles of a size sufficiently small to pass through the mouth and larynx upon inhalation and into the bronchi and alveoli of the lungs. Delivery of aerosolized therapeutics, particularly aerosolized antibiotics, is known in the art (see, for example U.S. Pat. No. 5,767,068 to VanDevanter et al., U.S. Pat. No. 5,508,269 to Smith et al., and WO 98/43,650 by Montgomery, all of which are incorporated herein by reference). A discussion of pulmonary delivery of antibiotics is also found in U.S. Pat. No. 6,014,969, incorporated herein by reference.

By a "therapeutically effective amount" of a compound of the invention is meant an amount of the compound which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). An effective amount of the compound described above may range from about 0.1 mg/Kg to about 500 mg/Kg, preferably from about 1 to about 50 mg/Kg. Effective doses will also vary depending on route of administration, as well as the possibility of co-usage with other agents. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

The total daily dose of the compounds of this invention administered to a human or other animal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

The compounds of the formulae described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.1 to about 500 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with pharmaceutically excipients or carriers to produce a single dosage form will vary depending upon the host treated and the particular mode of administration. A typical preparation will contain from about 5% to about 95% active compound (w/w). Alternatively, such preparations may contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

Synthetic Methods

A pyrimidine derivative of the formula I, or a pharmaceutically-acceptable salt thereof, may be prepared by any process known to be applicable to the preparation of chemically-related compounds. Suitable processes for making certain intermediates. Necessary starting materials may be obtained by standard procedures of organic chemistry. The preparation of such starting materials is described within the accompanying non-limiting Examples. Alternatively necessary starting materials are obtainable by analogous procedures to those illustrated which are within the ordinary skill of a chemist.

The compounds described herein will be better understood in connection with the following representative synthetic schemes that illustrate the methods by which the compounds of the invention may be prepared, which are intended as an illustration only and not limiting of the scope of the invention.

Scheme 1

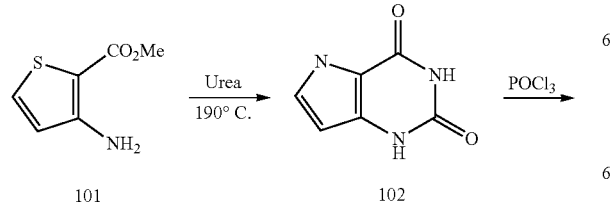

101  102

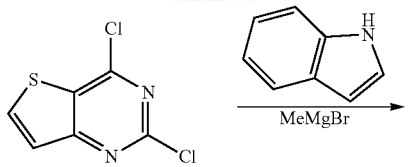

103

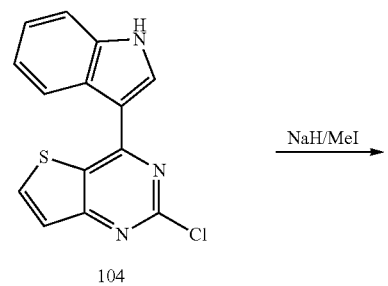

104

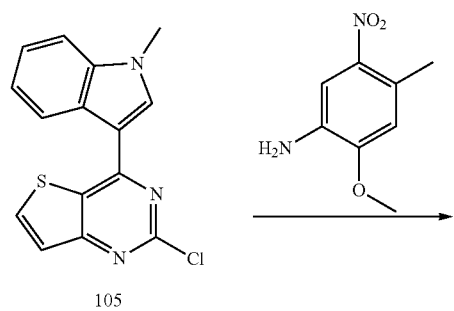

105

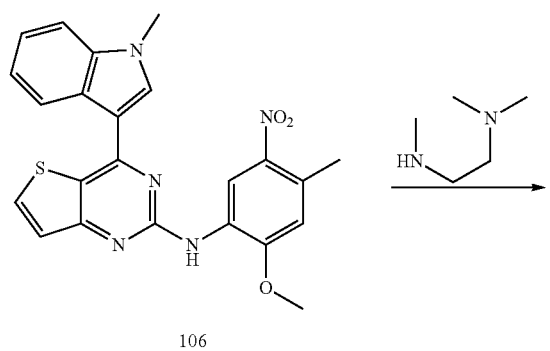

106

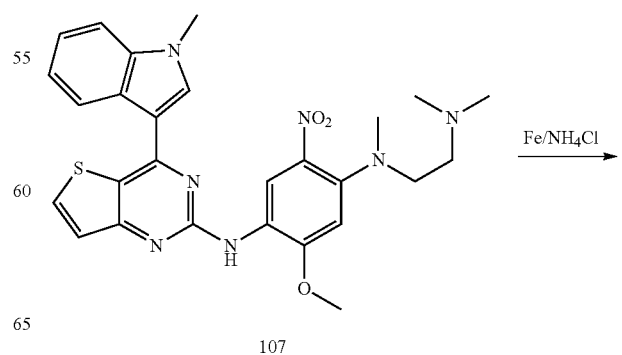

107

25
-continued

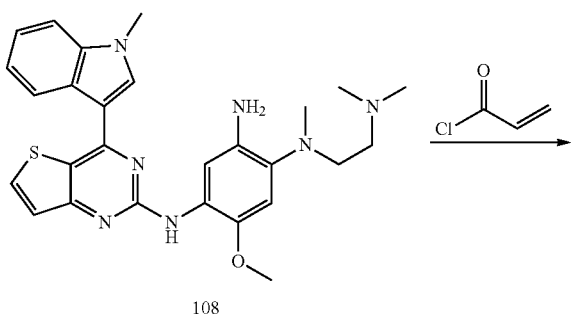

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Example 1: Synthesis of N-[2-[2-(dimethylamino) ethyl-methyl-amino]-5-[[4-(1H-indol-3-yl)thieno[3, 2-d]pyrimidin-2-yl]amino]-4-methoxy-phenyl]prop-2-enamide (Compound 1)

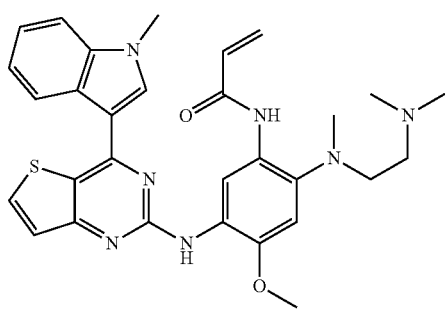

26

Synthesis of thieno[3,2-d]pyrimidine-2,4(1H,3H)-dione (Compound 102)

A mixture of methyl 3-amino-2-thiophenecarboxylate (13.48 g, 85.85 mmol) and urea (29.75 g, 0.43 mol) was heated at 190° C. for 2 h. Then the hot reaction mixture was poured into sodium hydroxide solution and insoluble material was removed by filtration. The mixture was then acidified by 2 N of HCl solution, collected by filtration and air dried, to give title compound (9.62 g, 67%) as a white precipitate.

Synthesis of 2,4-Dichlorothieno[3,2-d]pyrimidine (Compound 103)

Compound 102 (8.5 g) was suspended in phosphorous oxychloride (130 mL). The mixture was heated at 100° C. for 10 h. POCl3 was removed under reduced pressure. The mixture was dissolved in dichloromethane and quenched with ice. The product was collect by extraction with dichloromethane. The combined organic layers were dried over MgSO4 and concentrated to give product 103 as a white solid. LCMS: 205 [M+1]+; $^1$H NMR (400 MHz, CDCl$_3$): δ 7.48 (d, J=5.6 Hz, 1H), 8.05 (d, J=5.6 Hz, 1H).

Synthesis of 2-chloro-4-indol-3-ylthiopheno[3, 2-d]pyrimidine (Compound 104)

To a solution of indole (14 g, 120 mmol, 2 eq) in dry THF (60 mL) was added drop wise a mixture of methylmagnesium bromide (60 mL, 120 mmol, 2N, 2 eq) in THF below 5° C., and then the mixture was stirred at this temperature for 30 min. Then the suspension of 2,4-dichlorothiopheno[3,2-d]pyrimidine (12.4 g, 60 mmol, 1 eq) in 50 mL THE was added into the mixture below 5° C., and the mixture was stirred for 1 h, and then heated to 60° C. overnight. The reaction was quenched with acetic acid (8 mL, 13 mmol) and followed by addition of the water (100 mL). The precipitated solid was collected by filtration, washed with water, dried under vacuum to afford the product (9 g, 53%).

$^1$H NMR (300 MHz, DMSO-d6): δ12.22 (br, 1H), 8.59-8.66 (m, 1H), 8.51-8.53 (m, 1H), 8.42 (m, 1H), 7.50-7.61 (m, 2H), 7.23-7.38 (m, 2H); MS Calcd. 285.0 MS Found: 286.0 ([M+H]+).

Synthesis of 2-Chloro-4-(1-methylindol-3-yl)thieno [3,2-d]pyrimidine (Compound 105)

Sodium hydride (60% dispersion in mineral oil, 0.862 g, 21.54 mmol) was added to compound 104 (20.52 mmol) in THE (200 mL) at 0° C. under nitrogen. The resulting solution was stirred at 0° C. for 15 minutes. Methyl iodide (1.347 mL, 21.54 mmol) was added and the reaction was allowed to warm to room temperature and stirred for 2 hours. The reaction was incomplete so the reaction mixture was cooled again in an ice bath and further sodium hydride (0.862 g, 21.54 mmol) was added and the suspension was stirred at 0° C. for 10 minutes. Methyl iodide (1.347 mL, 21.54 mmol) was then added and the reaction stirred for an additional 1 hour. The reaction mixture was diluted with water (100 mL) and extracted with EtOAc (100 mL). The organics were washed with water (75 mL) and some solid formed at the solvent interface so the liquids were filtered and washed with water and ethyl acetate and the resultant solid dried to give 105 as a white solid (72% yield). MS Calcd. 298.09, MS Found: 299.9 ([M+H]+).

Synthesis of N-(4-fluoro-2-methoxy-5-nitro-phenyl)-4-(1-methylindol-3-yl)thieno[3,2-d]pyrimidin-2-amine (Compound 106)

p-Toluenesulfonic acid hydrate (1.4 g, 8.4 mmol, 1.2 eq) was added in one portion to a mixture of compound 105 (2 g, 7 mmol, 1 eq) and 4-fluoro-2-methoxy-5-nitroaniline (1.3 g, 7 mmol, 1 eq) in 2-pentanol (50 mL). The mixture was stirred at 130° C. overnight and then cooled to r.t. The precipitate was collected by filtration, washed with 2-pentanol (5 mL) and dried under vacuum to give some of the desired product as a yellow solid. The solid was recycled with MeOH to afford 0.9 g target compound 106. MS Calcd. 449.09, MS Found: 449.9 ([M+H]+).

Synthesis of N4-[2-(dimethylamino)ethyl]-2-methoxy-N4-methyl-N1-[4-(1-methylindol-3-yl)thieno[3,2-d]pyrimidin-2-yl]-5-nitro-benzene-1,4-diamine (Compound 107)

To a solution of compound 106 (300 mg) and N1,N1,N1-trimethylethane-1,2-diamine (75 mg) in DMF (4 ml) was added DIPEA (185 mg). The mixture was heated to 140° C. for 4 hours. The resulting mixture was cooled to room temperature and poured into water (10 ml), extracted with ethyl acetate (20 ml×3). The combined organic phases was washed with water, brine, dried with $Na_2SO_4$, filtered, and concentrated. The residue was purified by flash column to give a reddish solid (260 mg, 74% yield). MS Calcd: 531.2 MS Found: 532.1 ([M+H]+).

Synthesis of N1-[2-(dimethylamino)ethyl]-5-methoxy-N1-methyl-N4-[4-(1-methylindol-3-yl)thieno[3,2-d]pyrimidin-2-yl]benzene-1,2,4-triamine (Compound 108)

To a mixture of compound 107 (180 mg, 0.35 mmol), iron (78 mg, 1.4 mmol), and $NH_4Cl$ (1.4 mmol) was added a mixed solution of ethanol (4 ml) and water (2 ml). The resulting mixture was refluxed for 2 hours. The mixture was cooled to room temperature, filtered, concentrated. The residue was partitioned between DCM and water. The organic phase was washed with water, brine, and dried over $Na_2SO_4$, filtered, concentrated to give a crude product which was used in the next step directly without further purification. MS Calcd: 501.1 MS Found: 502.1 ([M+H]+).

Synthesis of N-[2-[2-(dimethylamino)ethyl-methyl-amino]-4-methoxy-5-[[4-(1-methylindol-3-yl)thieno[3,2-d]pyrimidin-2-yl]amino]phenyl]prop-2-enamide (Compound 1)

To a solution of compound 108 (90 mg, 0.18 mmol) in DCM (2 ml) was added DIPEA (0.22 mmol) at 0° C. followed by addition of acryloyl chloride (0.22 mmol). The mixture was stirred for 1 hour. The mixture was diluted with DCM (4 ml) and treated with $NaHCO_3$, extracted with DCM (3 ml×2). The combined organic phases was washed with water, brine, dried over $Na_2SO_4$, filtered, and concentrated. The residue was purified by flash column chromatography eluting with DCM/methanol=40/1 to give the desired product (30 mg, 33% yield).

$^1$H NMR (400 MHz, $CDCl_3$): δ 10.1 (s, 1H), 9.82 (s, 1H), 8.63 (m, 1H), 8.21 (s, 1H), 7.83 (m, 1H), 7.71 (s, 1H), 7.50 (m, 1H), 7.42 (m, 1H), 7.32-7.37 (m, 2H), 6.83 (s, 1H), 6.30-6.41 (m, 2H), 5.69-5.73 (m, 1H), 3.98 (s, 3H), 3.93 (s, 3H), 2.92 (m, 2H), 2.74 (s, 3H), 2.33 (m, 2H), 2.29 (s, 6H). MS Calcd: 555.1, MS Found: 556.1 ([M+H]).

Biological Assays

As stated hereinbefore the derivatives defined in the present invention possess anti-proliferation activity. These properties may be assessed, for example, using one or more of the procedures set out below:

1. EGFR Enzyme Assay

The following TABLE II lists compounds representative of the invention and their activity in EGFR assays. In these assays, the following grading was used: A: <0.1 μM; B: 0.1-10 μM.

TABLE II

| Compound # | T790M (IC50, μM) |
|---|---|
| 1 | A |
| 2 | A |
| 3 | A |
| 4 | B |
| 5 | A |
| 6 | A |
| 7 | B |
| 8 | A |
| 9 | A |

2. Efficacy Studies in Tumor Bearing Mice:

Female nu/nu mice were implanted with 1×10$^7$ NCI-H1975 cells in 50% Matrigel subcutaneously in the flank. Tumors were pair matched with a group size of 10 mice. Test compound was administrated orally at 40 mg/kg daily.

The values of tumor inhibition of selected compounds are shown in Table III.

TABLE III

| Compound # | Tumor growth inhibition (%) |
|---|---|
| 1 | >75 |
| 2 | >75 |
| 9 | >50 |

The invention has been illustrated by the above descriptions and examples. The examples are not intended to be limiting in any way. As used throughout, ranges are used as shorthand for describing each and every value that is within the range. Any value within the range can be selected as the terminus of the range. It is understood that when formulations are described, they may be described in terms of their ingredients, as is common in the art, notwithstanding that these ingredients may react with one another in the actual formulation as it is made, stored and used, and such products are intended to be covered by the formulations described. In addition, all references cited herein are hereby incorporated by reference in their entireties.

What is claimed is:

1. A compound represented by formula (I):

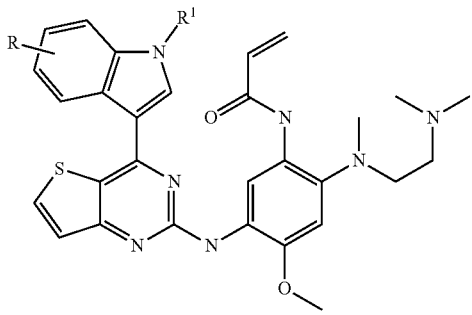

(I)

or by Formula (III)

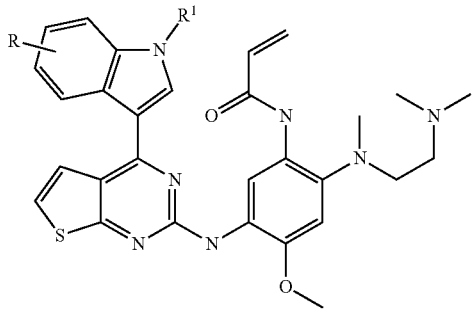

(III)

or its geometric isomers and a pharmaceutically acceptable salt and solvates thereof, wherein R and $R^1$ are independently H, halogen, SH, OH, $NO_2$, CN, $C_{1-6}$ alkyl, $C_{1-6}$ alkoxy, $C_{1-6}$ alkoxycarbonyl, $diC_{1-6}$ alkylamino$C_{2-6}$ alkylcarbonyl, amino, $C_{1-6}$ alkylamino, $diC_{1-6}$ alkylamino, carbamoyl, $C_{1-6}$ alkylcarbamoyl, di($C_{1-6}$ alkyl)carbamoyl, $diC_{1-6}$ alkylamino$C_{2-6}$ alkylcarbamoyl, sulfamoyl, $C_{1-6}$ alkylsulfonyl, $C_{1-6}$ alkylsulfinyl, $diC_{1-6}$ alkylamino$C_{2-6}$ alkylsulfamoyl, hydroxy$C_{2-6}$ alkoxy, hydroxycarbonyl$C_{1-6}$ alkyl, $C_{1-6}$ alkoxy$C_{1-6}$ alkyl, $diC_{1-6}$ alkylamino$C_{2-6}$ alkylamino, substituted $diC_{1-6}$ alkylamino$C_{2-6}$ alkylamino, amino$C_{1-6}$ alkyl, hydroxydi$C_{2-6}$ alkylamino, $C_{1-6}$ alkylamino$C_{2-6}$ alkoxy, $diC_{1-6}$ alkylamino$C_{2-6}$ alkoxy.

2. A compound according to claim 1, represented by formula (II):

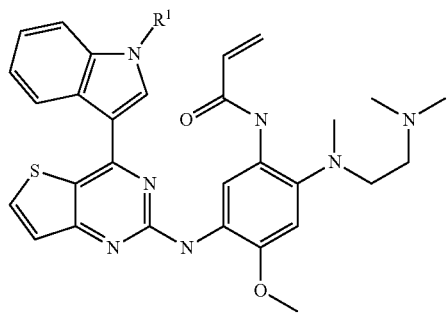

(II)

or its geometric isomers, enantiomers, diastereomers, racemates, pharmaceutically acceptable salts and solvates thereof.

3. A compound according to claim 1 represented by formula (III):

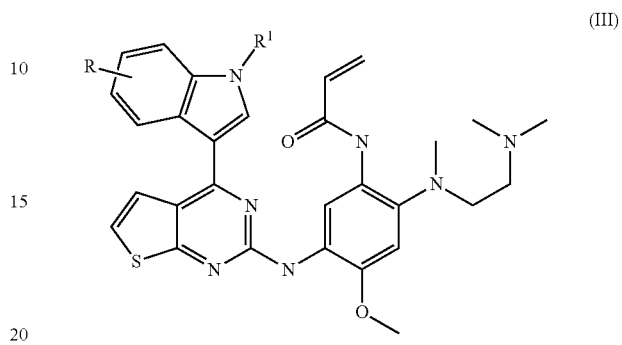

(III)

or its geometric isomers, enantiomers, diastereomers, racemates, pharmaceutically acceptable salts and solvates thereof.

4. A compound according to claim 1 represented by formula (IV):

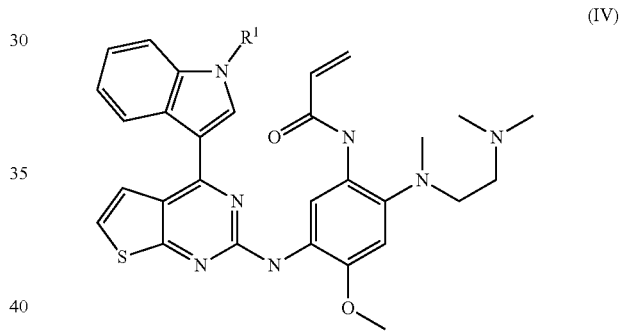

(IV)

or its geometric isomers, enantiomers, diastereomers, racemates, pharmaceutically acceptable salts and solvates thereof.

5. A compound selected from the group consisting of
N-[2-[2-(dimethylamino)ethyl-methyl-amino]-4-methoxy-5-[[4-(1-methylindol-3-yl)thieno[3,2-d]pyrimidin-2-yl]amino]phenyl]prop-2-enamide,
N-[2-[2-(dimethylamino)ethyl-methyl-amino]-5-[[4-(1-ethylindol-3-yl)thieno[3,2-d]pyrimidin-2-yl]amino]-4-methoxy-phenyl]prop-2-enamide,
N-[2-[2-(dimethylamino)ethyl-methyl-amino]-5-[[4-(1-isopropylindol-3-yl)thieno[3,2-d]pyrimidin-2-yl]amino]-4-methoxy-phenyl]prop-2-enamide,
N-[5-[[4-(1-tert-butylindol-3-yl)thieno[3,2-d]pyrimidin-2-yl]amino]-2-[2-(dimethylamino)ethyl-methyl-amino]-4-methoxy-phenyl]prop-2-enamide,
N-[2-[2-(dimethylamino)ethyl-methyl-amino]-5-[[4-(1,5-dimethylindol-3-yl)thieno[3,2-d]pyrimidin-2-yl]amino]-4-methoxy-phenyl]prop-2-enamide,
N-[2-[2-(dimethylamino)ethyl-methyl-amino]-4-methoxy-5-[[4-(5-methoxy-1-methyl-indol-3-yl)thieno[3,2-d]pyrimidin-2-yl]amino]phenyl]prop-2-enamide,
N-[2-[2-(dimethylamino)ethyl-methyl-amino]-4-methoxy-5-[[4-(6-methoxy-1-methyl-indol-3-yl)thieno[3,2-d]pyrimidin-2-yl]amino]phenyl]prop-2-enamide, N-[2-[2-(dimethylamino)ethyl-methyl-amino]-5-[[4-(1,6-dimethylindol-3-yl)thieno[3,2-d]pyrimidin-2-yl]amino]-4-methoxy-phenyl]prop-2-enamide, and N-[2-[2-(dimethylamino)ethyl-methyl-amino]-4-methoxy-5-[[4-(1-methylindol-3-yl)thieno[2,3-d]pyrimidin-2-yl]amino]phenyl]prop-2-enamide.

6. A pharmaceutical composition comprising an effective amount of a compound of claim 1, or a geometric isomer, enantiomer, diastereomer, racemate, pharmaceutically acceptable salt or solvate thereof, and a pharmaceutically acceptable excipient.

7. A compound represented by formula (I):

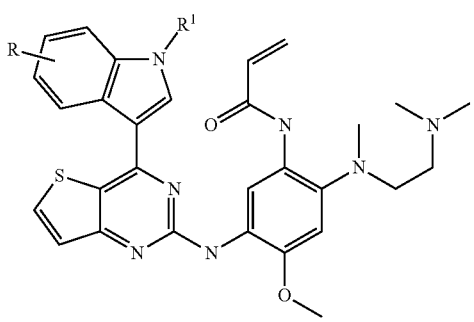

(I)

or by Formula (III)

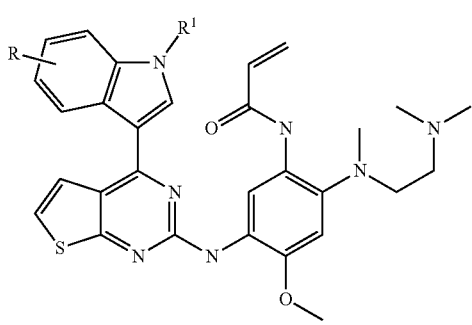

(III)

or its geometric isomers and a pharmaceutically acceptable salt and solvates thereof, wherein R is H, $C_{1-6}$ alkyl, or $C_{1-6}$ alkoxy; and $R^1$ is H or $C_{1-6}$ alkyl.

8. A pharmaceutical composition comprising an effective amount of a compound of claim 7, or a geometric isomer, enantiomer, diastereomer, racemate, pharmaceutically acceptable salt, or solvate thereof, and a pharmaceutically acceptable excipient.

9. A method for inhibiting the growth of a cancer cell which overexpresses the epidermal growth factor receptor (EGFR), comprising administering an effective amount of a compound of claim 1 to the cell.

10. A method for inhibiting the growth of a cancer cell according to claim 9, wherein the EGFR expressed by the cancer cell is a mutant EGFR.

11. A method for inhibiting the growth of a cancer cell according to claim 10, wherein the mutant EGFR is a T790M mutant, an L858R mutant or a delE746-A750 mutant.

12. A method for treating a human subject suffering from a disease in need thereof, wherein the disease is caused by abnormal cell proliferation, and the abnormal cell proliferation is caused by overexpression of EGFR, comprising administering to the subject a pharmaceutical composition of claim 6.

13. The method according to claim 12, wherein the abnormal cell proliferation is caused by overexpression of EGFR selected from the group consisting of ErbB1, ErbB32, ErbB3, and ErbB4.

14. The method according to claim 12, wherein the disease is a relapsed or acquired resistant malignant disease.

15. The method according to claim 12, wherein the subject is a human suffering from NSCLC.

16. A method for inhibiting the growth of a cancer cell which overexpresses the epidermal growth factor receptor (EGFR), comprising administering an effective amount of a compound of claim 7 the cell.

17. A method for treating a subject in need thereof, comprising administering to the subject a pharmaceutical composition of claim 14.

* * * * *